United States Patent [19]
Eickhorst

[11] 3,950,102
[45] Apr. 13, 1976

[54] ANALYSIS LAMP, PARTICULARLY FOR THE EXAMINATION OF PRECIOUS STONES

[76] Inventor: Manfred Eickhorst, Hans-Henny-Jahnn-Weg 21, 2 Hamburg 76, Germany

[22] Filed: Feb. 21, 1975

[21] Appl. No.: 551,678

[30] Foreign Application Priority Data
Feb. 26, 1974 Germany.................... 7406627[U]

[52] U.S. Cl.............. 356/73; 240/2.18; 240/103 R; 356/30; 356/51
[51] Int. Cl.².......................................... G01N 21/04
[58] Field of Search.............. 240/2.18, 103 R, 104; 356/30, 51, 73

[56] References Cited
UNITED STATES PATENTS
2,104,079  1/1938  Kahn..................................... 356/30
3,431,409  3/1969  Richter et al. .................. 240/103 R Primary Examiner—Vincent P. McGraw
Assistant Examiner—Richard A. Rosenberger
Attorney, Agent, or Firm—Thomas E. Beall, Jr.

[57] ABSTRACT

An analysis lamp, particularly for the examination of precious stones, with at least one daylight source and at least one UV light source, the observation planes for the light emitted by the daylight source and by the UV source being spatially separated from one another.

9 Claims, 1 Drawing Figure

U.S. Patent  April 13, 1976  3,950,102
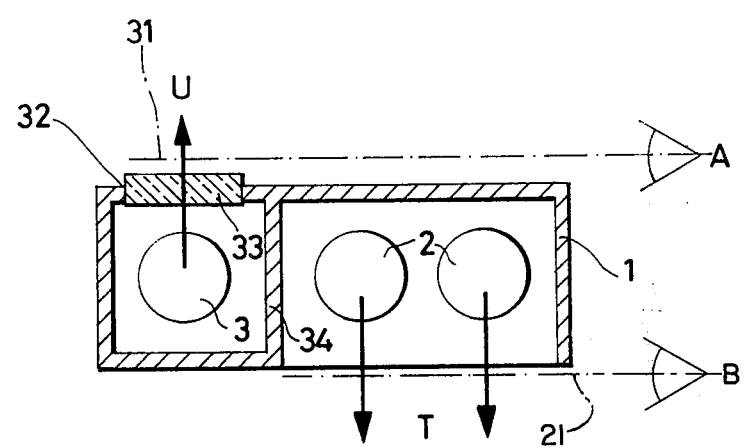

ANALYSIS LAMP, PARTICULARLY FOR THE EXAMINATION OF PRECIOUS STONES

BACKGROUND OF THE INVENTION

1. Field of Invention

The invention relates to an analysis lamp, particularly for the examination of precious stones, with at least one daylight source, and at least one UV light source.

2. Description of Prior Art

Known lamps of this kind, which are used by gemologists and jewellers for examinations of precious stones, are so constructed that a luminous discharge tube for daylight and a luminous discharge tube for UV light are arranged in a housing adjacent one another, only one of which may be switched on at a time and which shine in substantially the same direction. The housing is of course orientable and adjustable, nevertheless the work is normally carried out with the light shining from above onto the stones to be examined, the stones being held with tweezers and/or arranged in a groove of a V-shaped grading card suitable for colour comparison. In daylight which serves as a reference light, the stone is examined to judge the purity and colour of the stone while the fluorescence analysis is carried out in UV light to receive an indication of the nature of the stone, its chemical composition etc. and also to determine for example, when one is dealing with coloured stones, whether the stone in question is real or synthetic. It is necessary to provide a switch-over circuit for the daylight and UV light so that, when one is viewing a stone in one type of light, one can eleminate the influence of the other type of light. The requirement of continually changing over during the examination of large numbers of precious stones is an obstacle to a continuous flow of work.

3. Object of Invention

It is the main object of the invention to create a lamp of the type initially described with which the stones may be examined in a spatially most favourable layout and without any switching operations.

SUMMARY OF THE INVENTION

According to the invention in an analysis lamp for the examination of precious stones the observation planes for the light emitted by the daylight source and by the UV source are spatially separated from one another.

In a preferred form of the invention the two different light sources are in one common housing within which they are optically isolated from one another.

Such an arrangement makes it possible to switch the lamp on once and to carry out the examination under daylight and UV light without further switching operations and without the two different types of light affecting one another.

In a particularly advantageous embodiment of the invention the directions in which the two types of light shine are oriented at 180° to one another, resulting in that one is able to view from the optimal direction for whichever type of light is being used. In another particularly useful embodiment of the invention the aperture for the UV light is situated in the upper side of the lamp housing and covered by a UV suppression filter permitting the passage of UV light of one determined examination wavelength only. It is thus possible to carry out the examination by daylight in a substantially optimal manner so that the stone is held, for instance, in a folded grading card suitable for colour comparison in the downwardly shining light so that it is not necessary to look with the naked eye in the direction of the light illuminating the stone, but merely to observe the rays which are reflected in the stone in the viewing direction. Above all, this arrangement is advantageous, with respect to the UV examination, because the stone is placed on the filter and viewed at 90° to the direction of illumination with the result that the stone is seen in its fluorescent colour, completely uninfluenced by the UV light. It is known to be hazardous when the operator must look for long periods of time at UV light, particularly short wave UV light. According to the invention this hazard is completely avoided because the eye of the operator only receives fluorescent light, which is of a substantially greater wavelength.

One exemplified embodiment according to this invention will now be described in detail with reference to the accompanying schematic drawing.

BRIEF DESCRIPTION OF THE DRAWING

The drawing shows a cross section through a lamp housing.

DESCRIPTION OF THE PREFERRED EMBODIMENT

An analysis lamp, according to the invention, comprises a lamp housing 1 (also termed reflector) which is mounted on a support or stand, which is not shown in detail, so as to be pivotable and both vertically and laterally adjustable in a known per se manner. The lamp housing 1 is of rectangular box-like shape, which is here sectioned at a right angle to its longitudinal axis. In the lamp housing are two fluorescent tubes 2, which form the daylight source. The light produced by the two fluorescent tubes 2 radiates downwardly out of the lamp housing 1 in the direction of the arrow T. In addition to the two daylight fluorescent tubes 2 there is also provided a light source 3 (which is also tube-shaped) for the UV light. To prevent the UV light from influencing the daylight, a separating wall 34 is positioned in the lamp housing 1 between the daylight sources 2 and the UV source 3. The space in which the UV light source 3 is mounted is also sealed on its lower side so that the UV light can merely emerge in the direction of the arrow U. For this purpose an aperture for the emergence of the light 32 is provided in the lamp housing 1, this aperture being closed by a UV suppression filter 33 of the type which allows the passage of UV light of one determined and desired examination wavelength only, which in the present embodiment is that of 366 nm.

Working with the analysis lamp according to the invention is, as may be seen, both simple and practical. Both light sources 2 and 3 for producing the different types of light, daylight and UV light, can be on simultaneously and do not affect one another. One first of all holds the stone C under the daylight T in plane 21 and observes it from B at right angles to the direction of illumination T, for instance with the stone lying in the groove of a V-shaped grading card of folded white paper suitable for colour comparison. Finally the stone C in plane 31 is placed on the filter 33 and viewed from A at right angles to the direction of illumination U, in order to obtain the necessary information on its fluorescent properties. It is completely superfluous to switch off one or the other light source and then later to have to switch it on again, which fact results in a considerable increase in the operational life of the apparatus. The filter 33 also provides a practical surface on which the stone to be examined may be placed.

One can also see in the diagram the viewing planes which are represented by the dashed lines 31, for the UV light (the eye of the operator is shown at A) and 21 for the daylight (the eye of the operator is shown at B).

What I claim as my invention and desire to secure by Letters Patent is:

1. An analysis lamp, particularly for the examination of precious stones, with at least one artificial daylight source and at least one artificial UV light source, wherein the improvement comprises: means for establishing an observation plane for the light emitted by the daylight source and an observation plane for the light emitted by the UV source that is spatially separated from the daylight observation plane so that a stone may be viewed in the daylight observation plane without interference from the UV light source and viewed in the UV observation plane without interference by the daylight source with both sources emitting light.

2. The analysis lamp according to claim 1, including a common housing having partition means separating said daylight source and said UV light source to optically isolate them from each other.

3. The analysis lamp according to claim 2, wherein said housing has means, including said partition means, for establishing a directional beam of light from said UV light source and a directional beam of light from said daylight source, with the direction of orientation for said beams being approximately 180° from each other.

4. The analysis lamp according to claim 3, wherein the direction for the UV light source beam is generally vertically upward, and said housing includes a UV suppression filter means in the path of said UV light beam for permitting the passage of UV light of only one predetermined examination wavelength.

5. The analysis lamp according to claim 4, wherein said filter means provides an upwardly facing substantially horizontal surface on which a stone to be examined may be placed and viewed outside of said housing in an observation plane perpendicular to the UV light beam.

6. The analysis lamp of claim 1, having housing means, including said partition means for directionally establishing a light beam from said daylight source and a light beam from said UV source that is oriented substantially 180° with respect to the daylight beam.

7. A method of examining valuable stones, comprising the steps of: providing two separate beams of artificial daylight and artificial UV light that are oriented with respect to each other at a substantial angle; placing the stone to be examined in the UV light beam spatially removed from the daylight light beam and observing the thus illuminated stone within an observation plane substantially perpendicular to the UV light beam while the daylight beam is present; placing the stone to be examined in the daylight beam spatially removed from the UV light beam and observing the thus illuminated stone in an observation plane substantially perpendicular to the daylight beam, while said UV beam is present.

8. The method according to claim 7, wherein said light beams are oriented with respect to each other at substantially 180°.

9. The method of claim 8, wherein said UV beam is directed substantially vertically upward; and further including the step of filtering the UV beam with a UV suppression filter to pass only a single wavelength to the stone to be examined, and supporting the stone to be examined in the UV beam on the filter to be supported solely by the filter during examination with a UV beam.

* * * * *